US009349958B2

(12) United States Patent
Doudin et al.

(10) Patent No.: US 9,349,958 B2
(45) Date of Patent: May 24, 2016

(54) USE OF ZWITTERIONIC MOLECULES FOR FORMING A HOLE OR ELECTRON TRANSPORT LAYER

(75) Inventors: Bernard Doudin, Strasbourg (FR);
Pierre Braunstein, Strasbourg (FR);
Lucie Routaboul, Strasbourg (FR);
Guillaume Dalmas, Strasbourg (FR);
Zhengzheng Zhang, Lincoln, NE (US);
Peter Dowben, Trail Crete, NE (US)

(73) Assignees: CENTRE NATIONAL DE LA RECHERCHE SCIENTIFIQUE, Paris (FR); UNIVERSITE DE STRASBOURG, Strasbourg (FR); UNIVERSITY OF NEBRASKA LINCOLN, Lincoln, NE (US)

( * ) Notice: Subject to any disclaimer, the term of this patent is extended or adjusted under 35 U.S.C. 154(b) by 617 days.

(21) Appl. No.: 13/818,192

(22) PCT Filed: Aug. 23, 2011

(86) PCT No.: PCT/IB2011/053696
§ 371 (c)(1),
(2), (4) Date: Mar. 22, 2013

(87) PCT Pub. No.: WO2012/025878
PCT Pub. Date: Mar. 1, 2012

(65) Prior Publication Data
US 2013/0193426 A1 Aug. 1, 2013

(30) Foreign Application Priority Data

Aug. 24, 2010 (FR) ..................................... 10 03428

(51) Int. Cl.
*H01L 51/54* (2006.01)
*C09K 11/06* (2006.01)
*H01L 51/00* (2006.01)
*C07C 251/22* (2006.01)
*G03G 5/06* (2006.01)
*H01L 51/10* (2006.01)
*H01L 51/44* (2006.01)
*H01L 51/50* (2006.01)

(52) U.S. Cl.
CPC .......... *H01L 51/0032* (2013.01); *C07C 251/22* (2013.01); *G03G 5/0618* (2013.01); *H01L 51/0051* (2013.01); *H01L 51/105* (2013.01); *H01L 51/441* (2013.01); *H01L 51/5048* (2013.01); *H01L 51/5088* (2013.01); *Y02E 10/549* (2013.01); *Y02P 70/521* (2015.11)

(58) Field of Classification Search
None
See application file for complete search history.

(56) References Cited

U.S. PATENT DOCUMENTS

| 6,169,291 | B1 | 1/2001 | Metzger et al. |
| 2005/0025994 | A1 | 2/2005 | Hanna et al. |
| 2005/0211292 | A1 | 9/2005 | Chittibabu et al. |

FOREIGN PATENT DOCUMENTS

| FR | 2 877 337 | 5/2006 |
| WO | WO 2006/048547 | 5/2006 |

OTHER PUBLICATIONS

Routaboul et al. J. Am. Chem. Soc. 2012, 134, 8494-8506. Date of publication: Apr. 18, 2012.*
Machine translation of FR 2877337. Date of publication: May 5, 2006.*
International Search Report for PCT/IB2011/053696 dated Nov. 8, 2011.

* cited by examiner

*Primary Examiner* — Andrew K Bohaty
(74) *Attorney, Agent, or Firm* — B. Aaron Schulman, Esq.; Stites & Harbison, PLLC.

(57) ABSTRACT

The invention relates to the use of zwitterionic molecules for forming a hole or electron transport layer. The preferred zwitterionic molecules of the invention are derivatives of p-benzoquinonemonoimines. The invention is useful in the field of electronic devices in particular.

25 Claims, 3 Drawing Sheets

USE OF ZWITTERIONIC MOLECULES FOR FORMING A HOLE OR ELECTRON TRANSPORT LAYER

Figure 1:
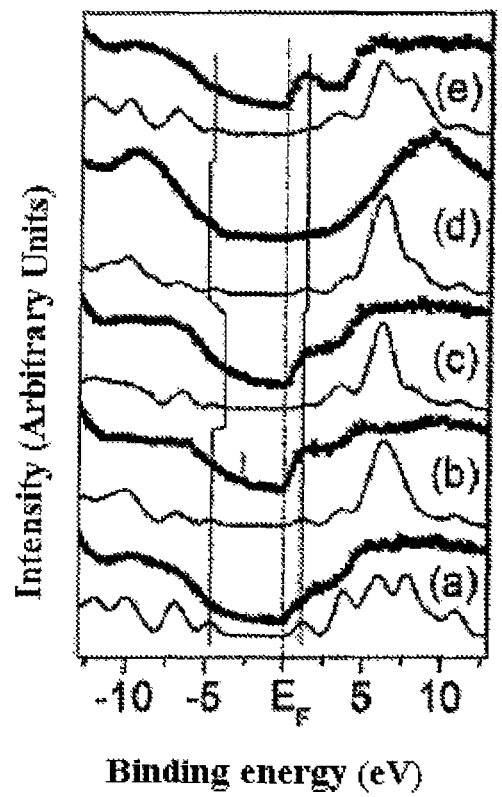

The invention relates to the use of molecules with a zwitterionic nature for the formation of hole or electron transport layers.

It also relates to a process for the manufacture of a layer of a substrate having hole or electron transport properties.

It also relates to such a substrate and to its uses.

Electronic devices of organic type today represent a major technological development in the electronic devices industry.

For example, organic light-emitting diode (OLED) screens have recently been introduced onto the consumer market.

They represent a considerable advance in terms of flexible electronic devices and of inexpensive conformational circuits.

This results in significant activity worldwide in the field of fundamental and applied research on organic electronic devices.

The major key players are mainly in Asia, the most important being Japanese and Korean companies.

In Europe, key developments are underway.

Even if the majority of devices currently marketed are obtained using vacuum evaporation techniques with sublimation of small molecules, there still exists a need for alternative solutions using wet chemical techniques in solution, these techniques having been successfully used for polymer-based devices.

The use of such techniques would make it possible to overcome the limitations due to the choice of the molecules and open the possibility for applications on the industrial scale which are less expensive.

Organic electronics involves mainly the use of semiconducting organic systems to create devices which mimic those, well known, using silicon technology, for example for diodes, transistors, current-light (light-emission) conversion devices and low-current devices (photovoltaic cell or light detector).

The most important systems are:

Organic Light-Emitting Devices (OLED):

In these devices, a current of a carrier is converted into emitted light. The structure of the device is a sequence of a vertical stack of:
- an anode of metal type (transparent side),
- a hole transport and injection layer,
- a recombination layer (emission),
- an electron transport and injection layer,
- a cathode of metal type.

Organic Photovoltaic (OPV) Devices:

The structure of these devices is similar to that of the OLEDs, with a different choice of materials, maximizing the efficiency of conversion of the incoming photons into electrical current.

Organic Transistors (OFET):

These devices are designed in lateral geometry (which explains the FET type of transistors envisaged).

In these devices, an organic film forms the active conducting layer between the metal source electrode and the metal drain electrode.

Control of the gate is normally obtained with a doped silicon substrate covered with $SiO_2$.

For all these systems, it is essential to ensure that a sufficient current flows.

This requires a limited interface barrier between the metal electrodes and the organic layer, and also good electron mobility of the charge carriers in the organic parts.

In the art, it is commonly accepted that one of the main bottlenecks during the practical use of such devices is the limited capability of the metal contacts to inject holes into the organic semiconductors, thus limiting the flow of the current (and, for example, the light outlet) of the resulting device.

This is especially critical for light-emitting devices.

Injection of holes is usually obtained by using materials having a low work function (for example $LaB_6$ and $GdB_6$) but more conventional electrode materials might be used when interfaces are well designed, for example $AuCu_3$, ITO (indium and tin oxide), TiAu or AlAu.

Nevertheless, a significant energy barrier systematically appears with the majority of electrode materials and this is to be overcome.

The key fundamental reason is the appearance of interface dipoles, resulting from a metal-organic charge imbalance creating surface dipoles at the interface.

The resulting electric field generally increases the height of the barrier for injecting the holes into an organic semiconductor, thus reducing the transport of the holes in the device.

Another highly desirable intrinsic property of organic conductors is the possibility of producing a good conductor carrying an electron charge (type n) as they are rarer in nature.

The invention is targeted at overcoming the disadvantages of the organic semiconducting films of the prior art and at providing molecular hole or electron transport systems.

It also makes it possible to obtain molecular interfaces having improved electronic properties.

To this end, the invention provides for the use of molecules with a zwitterionic nature having a strong intrinsic dipole, in particular having a dipole moment of greater than or equal to 10 debyes, in which there exists a charge delocalization within the anionic and cationic parts, for the formation of a hole or electron transport layer.

Molecules with a zwitterionic nature are characterized in that no neutral formula can describe them. There is thus a decoupling of residual + and − charges (zwei ions), resulting in an electric dipole. They are encountered, for example, in the fields of organic chemistry or organometallic chemistry.

Examples of organic zwitterionic molecules are:

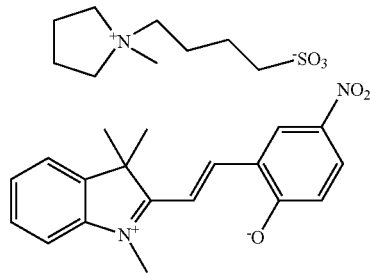

Examples of organometallic zwitterionic molecules are:

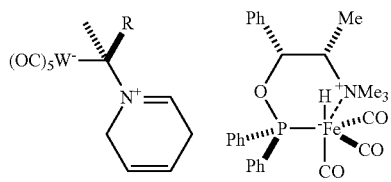

Preferably, the molecules with a zwitterionic nature are p-benzoquinone monoimine derivatives of following formula I:

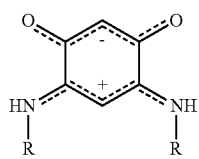

formula I in which R is chosen from:
H,
a linear or branched $C_1$ to $C_{20}$ alkyl radical which can be substituted by one or more radicals chosen from hydroxyl, amino, $C_1$ to $C_{12}$ aminoalkyl, $C_1$ to $C_{12}$ alkoxy, pyridine, phosphine, thioether, thiol, $C_1$ to $C_{12}$ alkene, $C_1$ to $C_{12}$ alkyne and halogen radicals, such as F, I, Br and Cl,
a benzyl radical which can be substituted by one or more radicals chosen from hydroxyl, amino, $C_1$ to $C_{12}$ aminoalkyl, $C_1$ to $C_{12}$ alkoxy and halogen radicals, such as F, I, Br and Cl.

More preferably, use is made of the derivatives of formula I in which R is chosen from a hydrogen atom or a $—C_4H_9$, $—C_3H_6—S—CH_3$, $—C_6H_5—CH_2—$ or $—C_3H_6—O—CH_3$ group.

Most preferably, use is made of the derivatives of formula I in which R is chosen from a $—C_4H_9$ group or a $—C_6H_5—CH_2—$ group.

According to one embodiment, the hole and electron transport layer formed by the molecules with a zwitterionic nature acts as a conducting electrode.

The invention also provides a process for the manufacture of a substrate having hole or electron transport properties, characterized in that it comprises the bonding, to at least one surface of a support, of at least one type of molecule with a zwitterionic nature.

The surface of the support can be a conducting layer, in particular a metal conducting layer (for example Au), an insulating layer (for example $SiO_2$, or a metal oxide having ferroelectric properties, such as $LiNbO_3$, or a material having end groups which react with oxides) or a semiconducting layer (for example $SiO_xH_y$), which can be obtained as a thin layer on a support compatible with microelectronic devices (for example, Si wafer covered with $SiO_2$).

In the process of the invention, preferably, the molecules with a zwitterionic nature are p-benzoquinone imine derivatives of following formula I:

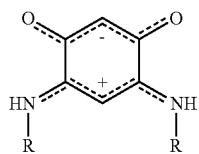

formula I in which R is chosen from:
H,
a linear or branched $C_1$ to $C_{20}$ alkyl radical which can be substituted by one or more radicals chosen from hydroxyl, amino, $C_1$ to $C_{12}$ aminoalkyl, $C_1$ to $C_{12}$ alkoxy, pyridine, phosphine, thioether, thiol, $C_1$ to $C_{12}$ alkene, $C_1$ to $C_{12}$ alkyne and halogen radicals, such as F, I, Br and Cl,
a benzyl radical which can be substituted by one or more radicals chosen from hydroxyl, amino, $C_1$ to $C_{12}$ aminoalkyl, $C_1$ to $C_{12}$ alkoxy and halogen radicals, such as F, I, Br and Cl.

However, more preferably, the derivatives of formula I are those in which R is chosen from a hydrogen atom or a $—C_4H_9$, $—C_3H_6—S—CH_3$, $—C_6H_5—CH_2—$ or $—C_3H_6—O—CH_3$ group.

Most preferably, the derivatives of formula I are those in which R is chosen from a $—C_4H_9$ group or a $C_6H_5—CH_2—$ group.

Preferably again, in the process of the invention, the material constituting the surface acting as electrode is preferably chosen from Al, Au, $AuCu_3$, ITO, TiAu, AlAu, graphene, $LaB_6$, $GdB_6$, Ni, Co, Fe, Pd, Pt, and the alloys of these different materials.

The invention also provides a substrate having hole or electron transport properties, characterized in that it comprises a support, at least one surface of which is made of a material chosen from Al, Au, $AuCu_3$, ITO, TiAu, AlAu, graphene, $LaB_6$, $GdB_6$, Ni, Co, Fe, Pd, Pt, and the alloys of these different materials, and in that a layer of at least one type of molecule with a zwitterionic nature is bonded to said surface.

The surface of the support can be a layer made of a conducting material, such as a metal, for example Au, or made of an insulating material, such as, for example, $SiO_2$ or $LiNbO_3$, or made of a semiconducting material, such as, for example, $SiO_xH_y$, which can be obtained as a thin layer on a support compatible with microelectronic devices, for example an Si wafer covered with $SiO_2$.

When the surface of the support is a layer made of an insulating or semiconducting material, the layer of at least one type of molecule with a zwitterionic nature can advantageously act as conducting electrode. In this context, the compounds with a zwitterionic nature of formula (I) in which R is a $C_6H_5—CH_2—$ group are particularly preferred.

Preferably, the layer of at least one type of molecule with a zwitterionic nature is formed of molecules of following formula I-1:

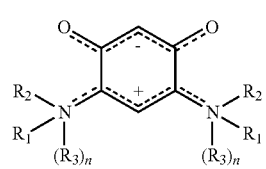

formula I-1 in which:
n=0 or 1, and
$R_1$ and $R_2$ are chosen from the following pairs:
when $R_1$ is:

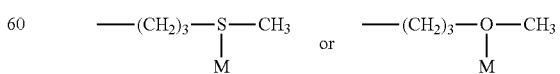

then $R_2$ is H and n=0,
when $R_1$ is $—C_4H_9$:
either $R_2$ is $H_2$ and n=1, in which case $R_3$ is M (nitrogen-metal interaction), or $R_2$ is H and n=1, in which case $R_3$ is M (nitrogen-metal interaction with deprotonation of the molecule on the surface), or $R_2$ is M and n=0, when $R_1$ is —$CH_2$—$C_6H_5$-M, then $R_2$ is H and n=0, when $R_1$ is —$CH_2$—$C_6H_5$:

either $R_2$ is H and n=1, in which case $R_3$ is M, or $R_2$ is M and n=0, in which M denotes an atom or a molecule of the material constituting the surface of the support.

Preferably, $R_1$ is chosen from a —$CH_2$—$C_6H_5$-M group or a group:

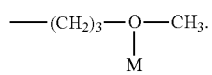

By way of illustration and without wishing to be committed to a specific theory, when the surface of the support is a layer made of a conducting material, M can in particular be a metal atom, for example an Au atom. When this surface is a layer made of an insulating material, M can in particular be a surface atom of a metal oxide, such as $LiNbO_3$. Finally, when this surface is a layer made of a semiconducting material, such as $SiO_xH_y$, M can be a hydrogen atom (hydrogen bond) or an oxygen atom.

The zwitterionic molecule of formula I-1 can be bonded to M present at the surface of the support via interactions with electron-rich groups present in its structure, such as heteroatoms having free pairs, in particular N, S or O, or also via aromatic groups (π interactions). These interactions generally resemble an electronic exchange between the zwitterionic molecule and the surface of the support (M group) and are typically characterized by an energy shift of approximately 0.5 eV.

The invention also provides a device comprising a substrate according to the invention or obtained by the process of the invention or by the use according to the invention.

In a first embodiment, the device is of the OLED type.

In a second embodiment, the device is of the OPV type.

In a third embodiment, the device is of the OFET type.

The invention also provides for the use of a substrate according to the invention or obtained by the process according to the invention or by the use according to the invention, as screen of the interface barrier of an electrode/molecular film system.

The invention also provides for the use of a substrate according to the invention or obtained by the process according to the invention or by the use according to the invention, as interface layer for a diode effect.

The invention also provides for the use of a substrate according to the invention or obtained by the process according to the invention or by the use according to the invention, as optically transparent layer having conducting properties.

Finally, the invention provides for the use of a substrate according to the invention or obtained by the process according to the invention or by the use according to the invention, as electrode having conducting properties.

Figure 2:
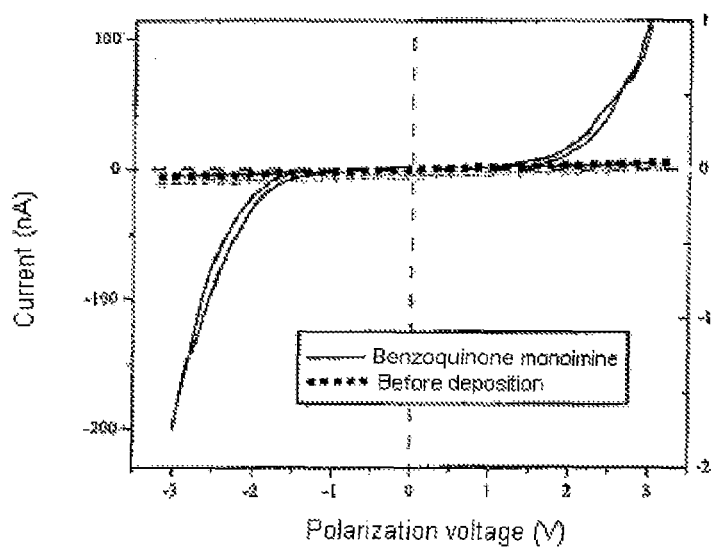
Figure 3:
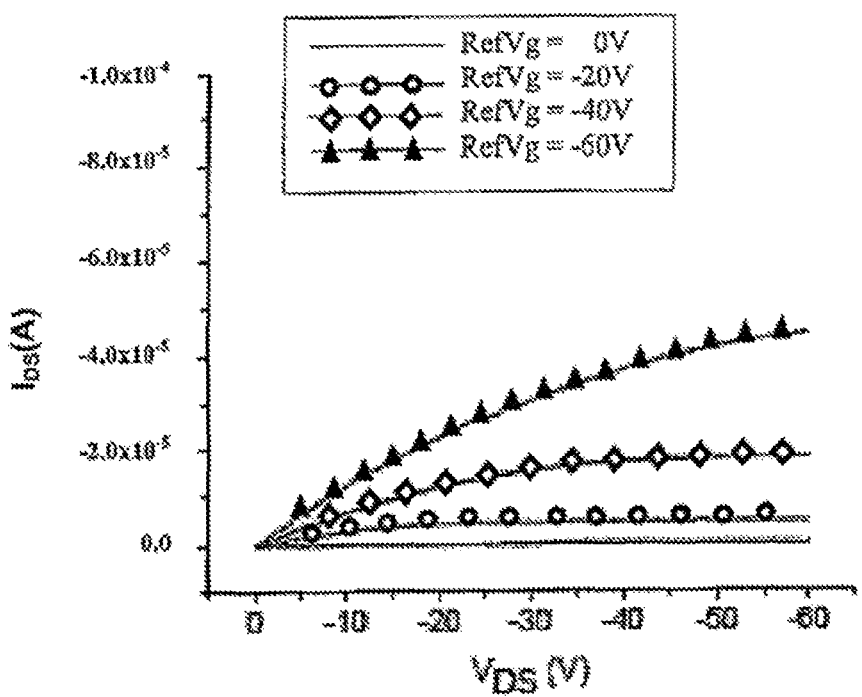
Figure 4:
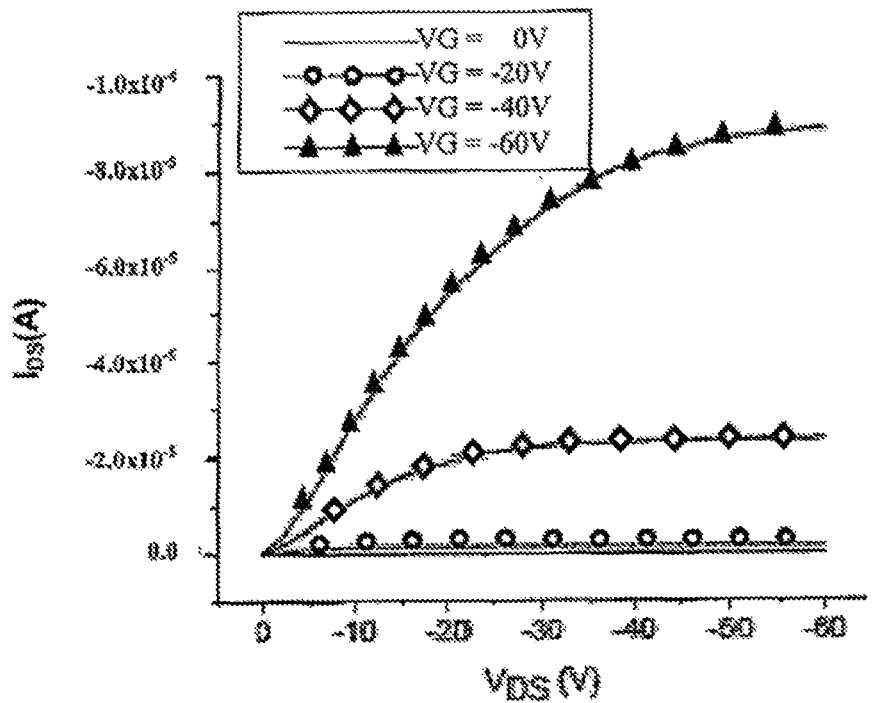
Figure 5:
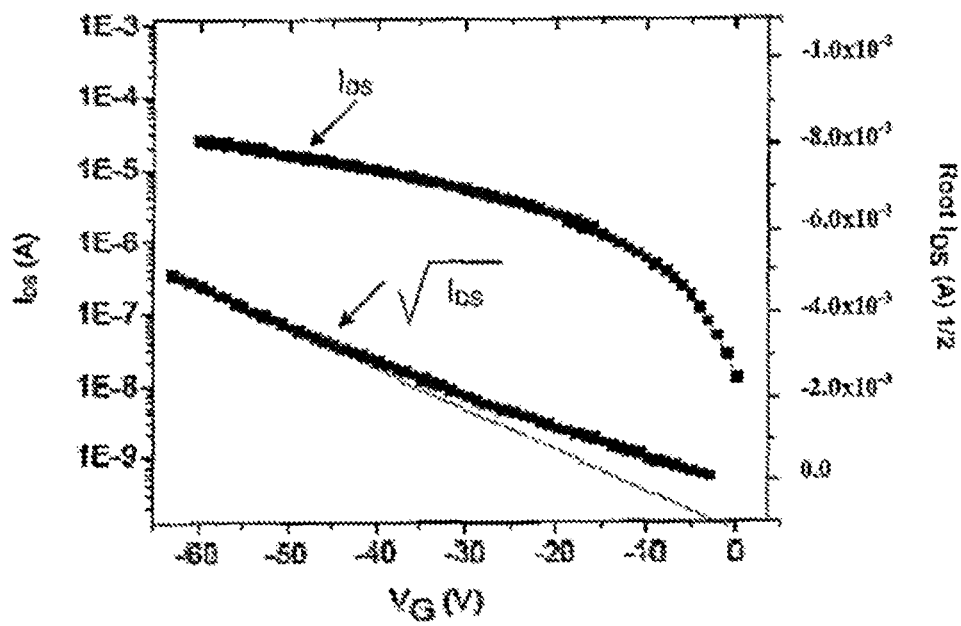
Figure 6:
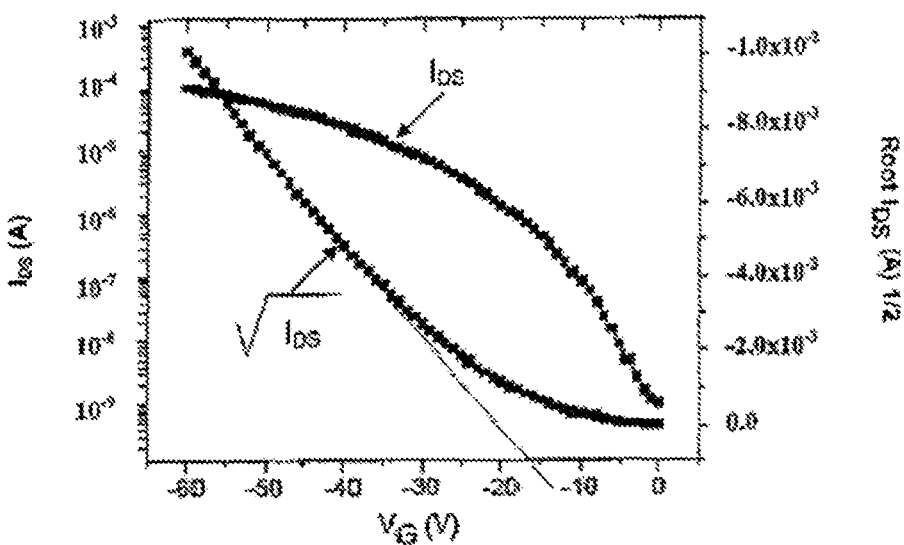

A better understanding of the invention will be obtained and other characteristics and advantages of the invention will become more clearly apparent in the light of the explanatory description which follows and with reference to the figures, in which:

FIG. 1 shows the combined photoemission and inverse photoemission spectra of the preferred zwitterionic molecules of the invention, FIG. 2 shows the flow of the current through a zwitterionic molecule (R=butyl $C_4H_9$ radical) according to the invention, in comparison with the loss of current without molecule, between two gold electrodes separated by 1 to 3 nanometers, FIG. 3 shows the output curves, that is to say the curves of variation in the intensity of the current between the source electrode and the drain electrode as a function of the voltage applied to the gate of an OFET according to the prior art, FIG. 4 shows the output curves, that is to say the curves of variation in the intensity of the current between the source electrode and the drain electrode as a function of the voltage applied to the gate of an OFET according to the invention, FIG. 5 represents the transfer curve, that is to say the curve representing the variation in the intensity between the source electrode and the drain electrode of an OFET according to the prior art, as a function of the voltage applied to the gate electrode of this OFET, and also the curve representing the root of this variation in intensity, and FIG. 6 represents the transfer curve, that is to say the curve of variation in the intensity of the current between the source electrode and the drain electrode of an OFET according to the invention, as a function of the voltage applied to the gate electrode of this OFET, and also the curve representing the root of this variation.

The invention relates to the use of molecules with a zwitterionic nature in order to form hole or electron transport layers.

The molecules with a zwitterionic nature have a significant intrinsic dipole, in particular a dipole moment of greater than 10 debyes, which plays a key role of interface screen and of adjustment of the HOMO (Highest Occupied Molecular Orbital) level on the edge of the conducting band of a substrate made of a semiconducting material.

Specifically, the inventors have discovered that the use of films (layers, surfaces) formed of molecules with a zwitterionic nature effectively and efficiently reduces the interface barrier, making it possible for the electrons created in the films to rapidly escape from the substrate made of (semiconducting) material, and that the holes created in the films can rapidly escape from the substrate made of a semiconducting material and that, furthermore, it is possible to obtain a non-zero density of the states of the molecular films at the Fermi level of the substrate made of a semiconducting material/film of metal molecules system.

Many families of molecules with a zwitterionic nature are known.

Mention may be made, as examples, of the following molecules:

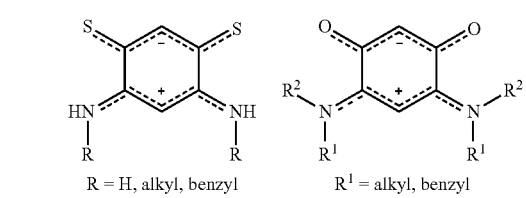

-continued

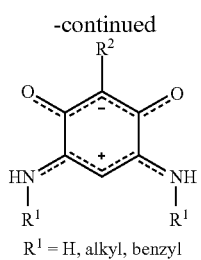

R¹ = H, alkyl, benzyl

However, a specific family of molecules with a zwitterionic nature is the molecules of the family of the p-benzoquinone monoimines of following formula I:

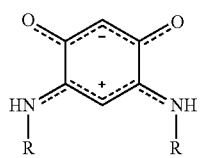

formula I in which R represents:
H,
a linear or branched $C_1$ to $C_{20}$ alkyl radical which can be substituted by one or more radicals chosen from hydroxyl, amino, $C_1$ to $C_{12}$ aminoalkyl, $C_1$ to $C_{12}$ alkoxy, pyridine, phosphine, thioether, thiol, $C_1$ to $C_{12}$ alkene, $C_1$ to $C_{12}$ alkyne and halogen radicals, such as F, I, Br and Cl,
a benzyl radical which can be substituted by one or more radicals chosen from hydroxyl, amino, $C_1$ to $C_{12}$ aminoalkyl, $C_1$ to $C_{12}$ alkoxy and halogen radicals, such as F, I, Br and Cl.

The archetypal molecule of formula I appears in the scheme below:

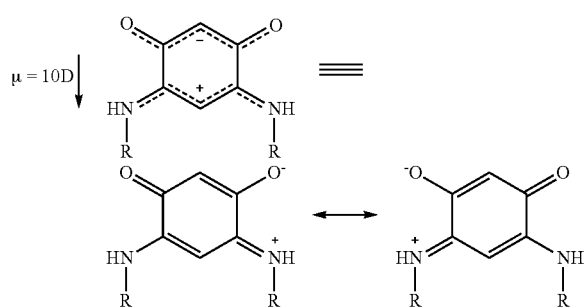

These small molecules have an intrinsic electric dipole of 10 debyes, which is high for such small molecules.

The nitrogen can be used to modify the end group R and thus to adjust the attachment to a surface.

The compounds of formula (I) can be prepared by any method known to a person skilled in the art and in particular according to the process described in WO 2006/048547.

The terms "bonded to the surface" and "bonding to the surface" are understood to mean, in the present invention, both grafting and adsorption. More specifically, it can be a chemical bond in which electrons of the zwitterionic molecule and of the material constituting the surface of the support are shared, but also weaker interactions or bonds of the following types: hydrogen bonds, Van der Waals interactions or electrostatic bonds of dipoles-dipoles type.

The oxygen groups can be used for coordination chemistry reactions, using a metal center to bond two molecules with a zwitterionic nature.

These molecules are known but as dye.

The experiments carried out by the inventors on these molecules have revealed that it is possible to bond these molecules to surfaces and to characterize their electronic properties.

Thus, these molecules make it possible to produce novel molecular systems bonded to surfaces.

These organic molecules have an intrinsic dipole which screens the harmful effect of the dipole of the metal interface.

It is possible with these molecules to deposit thin films covering more than 98% of the surface of a support made of a conducting material, such as gold (Au), indium tin oxide (ITO), an alloy of gold and copper ($AuCu_3$), an alloy of titanium and gold (TiAu) and an alloy of aluminum and gold (AlAu).

It is also possible to deposit thin films covering these molecules covering substrates which are nonconducting or only slightly conducting, such as silica ($SiO_2$) or lithium niobate ($LiNbO_3$), also having ferroelectric properties.

The properties of the films formed, in particular the fact that the electrons created in the films formed can rapidly escape from the substrate and that the holes created in the films formed can also escape from the substrate, show that these molecules transport the charge carriers very well and have limited interface barriers with the substrate.

This is extremely rare for molecules on surfaces.

Also, with these molecules, it is possible to obtain a non-zero density of the states of the molecular films at the Fermi level of the substrate made of a metal or semiconducting or insulating material/film of metal molecules system.

This property is noteworthy as, to the knowledge of the inventors, there have not existed to date organic systems in which the HOMO-LUMO (lowest unoccupied molecular orbital) gap corresponds as closely to the Fermi level of a conducting or semiconducting substrate.

Without wishing to be bound to a theory, the inventors attribute this exceptional property, making use of their knowledge of molecular orientations, to the intrinsic dipole of the molecules used in the invention.

The absence of resulting shift in the photoemission spectra is an immediate result of the significant conductivity of the molecular films thus formed, the only other example of which known to persons skilled in the art was graphite.

In order to achieve a better understanding of the invention, a description will now be given of several implementational examples thereof, purely by way of illustration and without implied limitation.

In the examples which follow, p-benzoquinone monoimine derivatives of formula I have been absorbed on substrates having a surface made of gold.

The gold surface, washed beforehand in a sequence of exposure to ethanol (in an ultrasonic bath) and acetone, is left for 16 h in a solution of the molecules. The solution generally has a concentration of 0.8 mol/l, the solvent used being mainly dichloromethane. The surface is washed several times with ethanol and then dried and stored under an inert atmosphere.

The thickness of the film obtained is between 0.5 and 1 nm inclusive, after intensive washing (10 minutes under a sustained stream of ethanol).

EXAMPLE 1

Use was made of a molecule of formula I in which R is H.

The combined inverse photoemission and photoemission spectra are denoted (a) in FIG. 1.

The schematic structure of the molecule, indicating the structure when adsorbed on the gold or otherwise bonded to the support made of gold, is a combination of the two following structures:

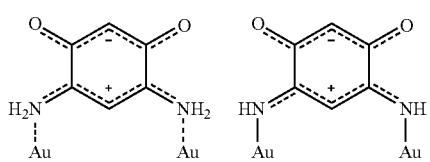

EXAMPLE 2

Use was made of a p-benzoquinone monoimine derivative of formula I in which R is $C_4H_9$.

The combined inverse photoemission and photoemission spectra of the film obtained are shown in FIG. 1, where they are denoted (b).

The structure of the compound of formula (I) used, when adsorbed on the gold or bonded to the surface made of gold of a support, is a combination of the following structures:

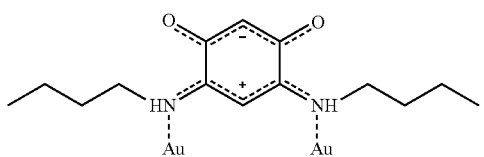

EXAMPLE 3

Use was made of a p-benzoquinone monoimine derivative of formula I in which R is $C_3H_6$—S—$CH_3$.

The spectra of inverse photoemission and of photoemission combined with the film thus formed are shown in FIG. 1, where they are denoted (c).

The structure of the molecules used, when adsorbed on the surface of the support made of gold, is as follows:

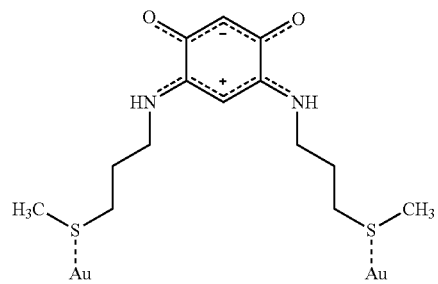

EXAMPLE 4

Use was made of a p-benzoquinone monoimine derivative of formula I in which R is $C_3H_6$—O—$CH_3$.

The combined inverse photoemission and photoemission spectra are represented in FIG. 1, where they are denoted (d).

The structure of these molecules, when adsorbed on the surface of a support made of gold, is as follows:

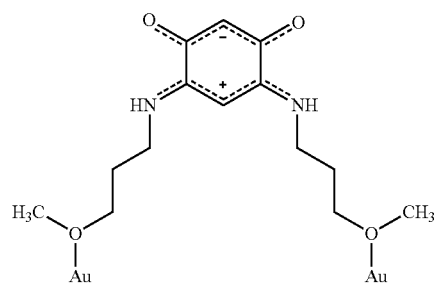

EXAMPLE 5

Use was made of a p-benzoquinone monoimine derivative of formula I in which R is $CH_2$—$C_6H_5$.

The combined inverse photoemission and photoemission spectra of the films obtained with this derivative are shown in FIG. 1, where they are denoted (e).

The structure of this derivative, when adsorbed on the surface of a support made of gold, is a combination of the following structures:

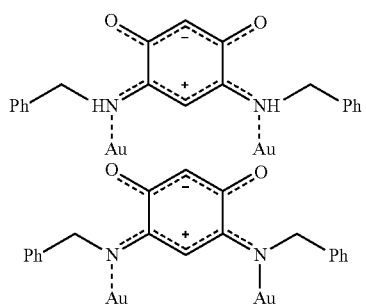

-continued

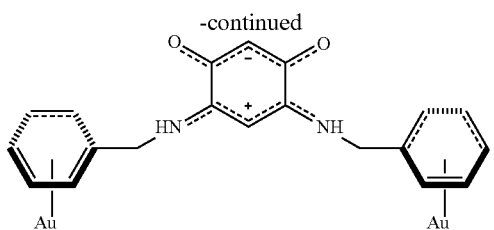

In FIG. 1, the combined inverse photoemission and photoemission spectra obtained with the film according to the invention are represented in thick lines while the theoretical density, obtained by models for the calculation of a single corresponding molecule, shown for comparison, is represented by a thin line.

EXAMPLE 6

The current flowing through a p-benzoquinone monoimine derivative of formula I in which R is $C_4H_9$ as a function of the voltage was also measured, in comparison with the leakage current without this derivative, between two gold electrodes separated by 1-3 nm.

These curves are represented in FIG. 2.

EXAMPLE 7

The work function of the device of example 2 was measured, along with that of a device identical to that of example 2 but to which a molecule of formula I in which R is a ethyl group is grafted, this being done in order to confirm that the presence of the compounds of formula I makes it possible to lower the work function in a way which is reproducible and stable over time.

For this, the electrons emitted by these devices were measured by UV photoelectron spectroscopy (UPS) at ambient pressure.

All the electrons emitted by the material, including the secondary electrons, are measured by UPS.

The work function corresponds to the start of detection of the photoemitted electrons.

By way of reference, the work function of a substrate made of gold, identical to that used to manufacture the samples used in the preceding examples and treated in the same way but to which no molecule was grafted, was measured under the same conditions.

The work function of the reference sample made of gold is 5.13 eV, the work function of the device of example 2 is 4.66 eV and the work function of the device in which the p-benzoquinone monoimine derivative of formula I in which R is an ethyl group is between 4.72 eV and 4.80 eV.

These measurements were carried out immediately after the manufacture of the device.

Thus, the difference between the work function of the reference sample, 5.13 eV, and those of the thin gold films to which the molecules of formula I of the invention have been grafted is approximately from 0.3 to 0.4 eV, in reproducible fashion. This shows that indeed the molecules of the invention make it possible to lower the work function and clearly shows the interface dipole screening effect of these molecules.

The reference sample and the sample of example 2 were left for four days in ambient atmosphere, that is to say in ambient air and in ambient humidity.

The work function was again measured.

The work function of the reference sample had not changed (it was still 5.13 eV after these four days) and the work function of the sample of example 2 was 4.72 eV.

This clearly shows that the molecules of formula I, when grafted to a surface made of gold, remain stable, that is to say are not decomposed, and remain grafted.

Results

It is seen, from FIG. 2, that the p-benzoquinone monoimine derivative of formula I in which R is a butyl (—$C_4H_9$) group has an excellent stacking density, complete covering of a metal substrate when ultrathin layers are obtained, and shows electrical conduction properties between two metal electrodes.

For these reasons, this p-benzoquinone monoimine derivative is a preferred compound for use in the invention.

It is seen, from FIG. 1, that the p-benzoquinone monoimine derivative with the highest level of electron mobility is the compound of formula I in which R is a benzyl group.

Furthermore, with this compound, no electrostatic charging effect was found during long-term irradiation with photons.

For this reason, this derivative is particularly preferred for use in the invention.

It is seen, from the above, that another subject matter of the invention is a process for the manufacture of a substrate having hole or electron transport properties which comprises the bonding, to at least one surface made of a preferably conducting material of a support, of at least one type of molecule with a zwitterionic nature.

In the process of the invention, preferably, the molecules with a zwitterionic nature are p-benzoquinone imine derivatives of following formula I:

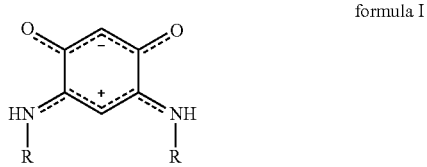

formula I in which R represents:
H,
a linear or branched $C_1$ to $C_{20}$ alkyl radical which can be substituted by one or more radicals chosen from hydroxyl, amino, $C_1$ to $C_{12}$ aminoalkyl, $C_1$ to $C_{12}$ alkoxy, pyridine, phosphine, thioether, thiol, $C_1$ to $C_{12}$ alkene, $C_1$ to $C_{12}$ alkyne and halogen radicals, such as F, I, Br and Cl,
a benzyl radical which can be substituted by one or more radicals chosen from hydroxyl, amino, $C_1$ to $C_{12}$ aminoalkyl, $C_1$ to $C_{12}$ alkoxy and halogen radicals, such as F, I, Br and Cl.

Preferably, in the formula I, R is chosen from a hydrogen atom or a —$C_4H_9$, —$C_3H_6$—S—$CH_3$, $C_6H_5$—$CH_2$— or —$C_3H_6$—O—$CH_3$ group.

More preferably, in the formula I, R is chosen from a —$C_4H_9$ group or a $C_6H_5$—$CH_2$— group.

With regard to the material, it is preferably chosen from Al, Au, $AuCu_3$, ITO, TiAu, AlAu, graphene, $LaB_6$, $GdB_6$, Ni, Co, Fe, Pd, Pt, and the alloys of these different materials.

By this process and using these molecules with a zwitterionic nature, a substrate is obtained having hole or electron transport properties.

This substrate is also a subject matter of the invention.

It comprises a support, at least one surface of which is made of a material chosen from Al, Au, AuCu$_3$, ITO, TiAu, AlAu, graphene, LaB$_6$, GdB$_6$, Ni, Co, Fe, Pd, Pt, and the possible alloys of these different materials, a layer of at least one type of molecule with a zwitterionic nature being bonded to said surface.

Preferably, the layer of at least one type of molecule with a zwitterionic nature is formed of molecules of following formula I-1:

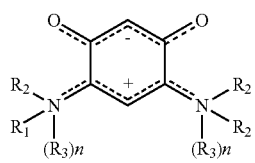

formula I-1 in which:
n=0 or 1, and
R$_1$ and R$_2$ are chosen from the following pairs:
when R$_1$ is:

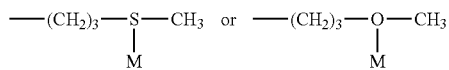

then R$_2$ is H and n=0,
when R$_1$ is —C$_4$H$_9$:
either R$_2$ is H$_2$ and n=1, in which case R$_3$ is M (nitrogen-metal interaction),
or R$_2$ is H and n=1, in which case R$_3$ is M (nitrogen-metal interaction with deprotonation of the molecule on the surface),
or R$_2$ is M and n=0,
when R$_1$ is —CH$_2$—C$_6$H$_5$-M, then R$_2$ is H and n=0,
when R$_1$ is —CH$_2$—C$_6$H$_5$:
either R$_2$ is H and n=1, in which case R$_3$ is M (nitrogen-metal interaction)
or R$_2$ is M and n=0 (deprotonation of the molecule on the surface),
in which M denotes an atom or a molecule of the material constituting the surface of the support.

This substrate was successfully used as interface barrier screen of an electrode/molecular film system, as interface layer for a diode effect and as optically transparent layer having conducting properties.

It has thus been incorporated in a device, such as a device of the OLED type, of the OPV type and of the OFET type.

These uses and devices are also subject matters of the invention.

EXAMPLE 8 (COMPARATIVE)

An OPV device of the prior art was manufactured.

For this, the surface of a substrate made of glass was covered with an ITO layer.

A layer of poly(3,4-ethylenedioxythiophene)-poly(styrenesulfonate) (PEDOT-PSS) was deposited on the free surface of this ITO layer.

An organic layer composed of a mixture, in a ratio by weight of 1:1, of poly(3-hexylthiophene) (P3HT) and of phenyl C61-butyric acid methyl ester (PCBM) was deposited on the free surface of this PEDOT-PSS layer.

This organic layer is subsequently coated with a layer of aluminum.

This OPV device configuration is the archetype of the best organic photovoltaic cells known to date.

The measured efficiency of this cell is 2.47625.

The mean current density of this cell is 7.512857 milliamperes/cm$^2$.

Nevertheless, this type of cell has a disadvantage: the ITO layer can be decomposed over time by the PEDOT-PSS.

EXAMPLE 9

A cell of OPV type was manufactured in the same way as in example 8 but, before depositing the PEDOT-PSS layer, zwitterionic molecules according to the invention of formula I in which R is a butyl group were grafted.

The efficiency of this cell is 2.62625.

The mean current density of this cell is 7.972 milliamperes/cm$^2$.

It is seen, from examples 8 and 9, that the grafting of the molecules of formula I according to the invention makes it possible to improve all of the properties of an OPV cell, both in terms of efficiency and of current density, and furthermore makes it possible to protect the ITO layer from the decomposing effect of the PEDOT-PSS layer.

EXAMPLE 10 (COMPARATIVE)

An organic transistor having a thin film of OFET type was manufactured.

For this, a layer of a dielectric material (in this case SiO$_2$) was deposited on a substrate made of p-doped silicon (which constitutes the gate of the transistor).

Two electrodes, a source electrode and a drain electrode, were deposited on the layer of dielectric material, and the dielectric material and the source and drain electrodes were covered with a layer which renders the substrate hydrophobic, in this example a layer of hexamethyldisilazane (HMDS).

Finally, an active layer of P3HT was deposited.

The variation in the intensity of the current moving between the source and drain electrodes, denoted I$_{DS}$, as a function of the voltage applied to the gate was measured.

The results are represented in FIG. 3 (output curve) and in FIG. 4 (transfer curve).

The mobility of the semiconducting channel was deduced from the results of the output curve.

The ION/IOFF ratio was determined from the results of the transfer curve.

The results for three samples, tested and manufactured under the same conditions, are given in table 1 below:

TABLE 1

| Sample | $\mu_{sat}$ (cm$^2$/V · s) | ION/IOFF |
|---|---|---|
| 1 | 3.7 × 10$^{-3}$ | 1.8 × 10$^{+2}$ |
| 2 | 3.13 × 10$^{-3}$ | 4.8 × 10$^{+2}$ |
| 3 | 3.6 × 10$^{-3}$ | 5.3 × 10$^{+2}$ |

It is seen, from table 1, that the mobility $\mu_{sat}$ varies between 3.13×10$^{-3}$ cm$^2$/V·s and 3.7×10$^{-3}$ cm$^2$/V·s.

The ION/IOFF ratio, which is representative of the interruption ratio of the transistor manufactured, for its part varies between 1.8×10$^{+2}$ and 5.3×10$^{+2}$.

It is found, from FIG. 3, that the maximum current $I_{Ds}$ is obtained for a voltage applied to the gate of −60 V and remains less than −4.0×10⁻⁵ A.

EXAMPLE 11

An OFET device was manufactured in the same way as in example 10, except that zwitterionic molecules according to the invention having the formula I in which R is a butyl group was grafted over the whole of the dielectric material and source and drain electrodes, before the deposition of the organic semiconducting layer.

It is normally not recommended to deposit charge-carrying molecules on the dielectric material as this reduces its interface properties with the semiconducting channel.

However, in this example, despite the disadvantage of depositing charge-carrying molecules on the dielectric material, a device was obtained having improved properties in terms of mobility of the electrons and of ION/IOFF ratio.

Specifically, the mobility and the ION/IOFF ratio of this device were measured.

The results obtained on three samples, tested and manufactured under the same conditions, are given in table 2 below:

TABLE 2

| Sample | $\mu_{sat}$ (cm²/V · s) | ION/IOFF |
|---|---|---|
| 1 | 5.3 × 10⁻³ | 4.1 × 10⁺⁴ |
| 2 | 1.2 × 10⁻³ | 2.04 × 10⁺⁴ |
| 3 | 1.4 × 10⁻² | 1.05 × 10⁺⁵ |

As is seen from table 2, the mobility varies between 1.2× 10⁻² and 1.4×10⁻² cm²/V·s and the ION/IOFF ratio varies between 2.04×10⁴ and 1.05×10⁵, which represents a significant improvement with respect to the OFET cell of the prior art.

Furthermore, the current $I_{DS}$ as a function of the voltage applied to the gate was measured for the OFET obtained in example 10 and for the OFET obtained in example 11.

The results are represented in FIGS. 5 and 6.

As is seen on comparing FIGS. 5 and 6, the current moving between the electrodes is much higher in the case of the OFET device according to the invention: it reaches a maximum of greater than −8.0×10⁵ for a gate voltage of 60 V.

Thus, by using the molecules of formula I of the invention, the mobility of the OFETs is increased by a factor of 2 and the ION/IOFF ratio is increased by nearly 2 orders of magnitude.

A particular advantage is the quiescent current, that is to say the current when the voltages between the source and drain electrodes and the gate voltages are all zero. The devices according to the invention systematically show a weaker current, which indicates a better ohmic behavior at low applied voltage, due to the better alignment of the energy levels at the metal-organic semiconductor interface.

A lower residual current between the source and drain electrodes is advantageous in terms of energy losses when the transistor is not active.

A higher saturation current between the source and drain electrodes is advantageous in terms of power applications of the transistor.

The invention claimed is:

1. A process for forming a hole or electron transport layer comprising a step of depositing on a surface of a substrate at least one monoimine derivatives of following formula I:

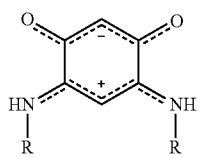

formula I in which R represents:
   H,
   a linear or branched $C_1$ to $C_{20}$ alkyl radical which can be substituted by one or more radicals selected from the group consisting of hydroxyl, amino, $C_1$ to $C_{12}$ aminoalkyl, $C_1$ to $C_{12}$ alkoxy, pyridine, phosphine, thioether, thiol, $C_1$ to $C_{12}$ alkene, $C_1$ to $C_{12}$ alkyne and halogen radicals,
   a benzyl radical which can be substituted by one or more radicals selected from the group consisting of hydroxyl, amino, $C_1$ to $C_{12}$ aminoalkyl, $C_1$ to $C_{12}$ alkoxy and halogen radicals.

2. The process as claimed in claim 1, wherein, in the formula I, R is chosen from a hydrogen atom or a —$C_4H_9$, —$C_3H_6$—S—$CH_3$, $C_6H_5$—$CH_2$— or —$C_3H_6$—O—$CH_3$ group.

3. The process as claimed in claim 1, wherein, in the formula I, R is chosen from a —$C_4H_9$ group or a $C_6H_5$—$CH_2$— group.

4. A process for the manufacture of a substrate having hole or electron transport properties, characterized in that it comprises the bonding, to at least one surface made of a conducting material of a support, of at least one p-benzoquinone imine derivative of following formula I:

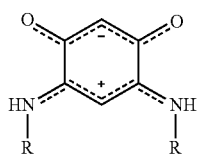

formula I in which R represents:
   H,
   a linear or branched $C_1$ to $C_{20}$ alkyl radical which can be substituted by one or more radicals chosen from hydroxyl, amino, $C_1$ to $C_{12}$ aminoalkyl, $C_1$ to $C_{12}$ alkoxy, pyridine, phosphine, thioether, thiol, $C_1$ to $C_{12}$ alkene, $C_1$ to $C_{12}$ alkyne and halogen radicals,
   a benzyl radical which can be substituted by one or more radicals chosen from hydroxyl, amino, $C_1$ to $C_{12}$ aminoalkyl, $C_1$ to $C_{12}$ alkoxy and halogen radicals.

5. The process as claimed in claim 4, characterized in that, in the formula I, R is chosen from a hydrogen atom or a —$C_4H_9$, —$C_3H_6$—S—$CH_3$, $C_6H_5$—$CH_2$— or —$C_3H_6$—O—$CH_3$ group.

6. The process as claimed in claim 4, characterized in that, in the formula I, R is chosen from a —$C_4H_9$ group or a $C_6H_5$—$CH_2$— group.

7. The process as claimed in claim 4, characterized in that the surface is made of a material chosen from Al, Au, AuCu$_3$, ITO, TiAu, AlAu, graphene, LaB$_6$, GdB$_6$, Ni, Co, Fe, Pd, Pt, and the alloys of these different materials.

8. A device comprising a substrate obtained by the process as claimed in claim 4.

9. The device as claimed in claim 8, characterized in that it is a device of the OLED type.

10. The device as claimed in claim 8, characterized in that it is a device of the OPV type.

11. The device as claimed in claim 8, characterized in that it is a device of the OFET type.

12. The substrate obtained by the process as claimed in claim 4, wherein said substrate is an interface barrier screen of an electrode/molecular film system.

13. The substrate obtained by the process as claimed in claim 4, wherein said substrate is an interface layer for a diode effect.

14. The substrate obtained by the process as claimed in claim 4, wherein said substrate is an optically transparent layer having conducting properties.

15. The substrate obtained by the process as claimed in claim 4, wherein said substrate is an electrode having conducting properties.

16. A substrate having hole or electron transport properties, characterized in that it comprises a support, at least one surface of which is made of a material chosen from Al, Au, AuCu$_3$, ITO, TiAu, AlAu, graphene, LaB$_6$, GdB$_6$, Ni, Co, Fe, Pd, Pt, and the alloys of these different materials, and in that a layer of at least one type of molecule of following formula I-1:

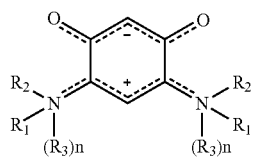

formula I-1 in which:
n=0 or 1, and
R$_1$ and R$_2$ are chosen from the following pairs:
R$_1$ is:

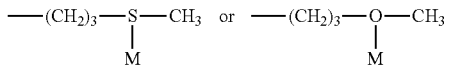

in which case R$_2$ is H and n=0,
R$_1$ is —C$_4$H$_9$, in which case:
either R$_2$ is H and n=1, in which case R$_3$ is M,
or R$_2$ is M and n=0,
R$_1$ is —CH$_2$—C$_6$H$_5$-M, in which case R$_2$ is H and n=0,
R$_1$ is —CH$_2$—C$_6$H$_5$, in which case:
either R$_2$ is H and n=1, in which case R$_3$ is M,
or R$_2$ is M and n=0,
in which M denotes an atom or a molecule of the material of which said surface of the support is composed, is bonded to said surface.

17. The substrate as claimed in claim 16, characterized in that, in the formula I-1, R$_1$ is chosen from a —CH$_2$—C$_6$H$_5$-M group or a group:

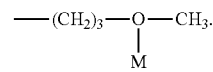

18. A device comprising a substrate as claimed in claim 16.

19. The device as claimed in claim 18, characterized in that it is a device of the OLED type.

20. The device as claimed in claim 18, characterized in that it is a device of the OPV type.

21. The device as claimed in claim 18, characterized in that it is a device of the OFET type.

22. The use of a substrate as claimed in claim 16, wherein said substrate is an interface barrier screen of an electrode/molecular film system.

23. The use of a substrate as claimed in claim 16, wherein said substrate is an interface layer for a diode effect.

24. The use of a substrate as claimed in claim 16, wherein said substrate is an optically transparent layer having conducting properties.

25. The use of a substrate as claimed in claim 16, wherein said substrate is an electrode having conducting properties.

* * * * *